United States Patent
Houser et al.

[11] Patent Number: 5,855,552
[45] Date of Patent: Jan. 5, 1999

[54] CATHETER HAVING RING ELECTRODES SECURED THEREON

[75] Inventors: Russell A. Houser, Livermore; Gloria Alvarez, Tracy; Russell B. Thompson, Los Altos; Michael Idaomi, Sunnyvale, all of Calif.

[73] Assignee: EP Technologies, Inc., Sunnyvale, Calif.

[21] Appl. No.: 876,114

[22] Filed: Jun. 13, 1997

Related U.S. Application Data

[60] Continuation of Ser. No. 558,955, Nov. 13, 1995, abandoned, which is a division of Ser. No. 304,754, Sep. 21, 1994, Pat. No. 5,524,337.

[51] Int. Cl.$^6$ .............................. A61B 5/042; A61B 17/39
[52] U.S. Cl. .......................... 600/374; 600/393; 606/41; 607/122
[58] Field of Search ........................................ 600/373–381, 600/393; 607/122, 119, 123, 117, 116; 606/41

[56] References Cited

U.S. PATENT DOCUMENTS

| | | | |
|---|---|---|---|
| 2,472,485 | 6/1949 | Krippendorf . | |
| 3,416,531 | 12/1968 | Edwards . | |
| 3,485,234 | 12/1969 | Stevens . | |
| 3,924,632 | 12/1975 | Cook . | |
| 4,035,534 | 7/1977 | Nyberg . | |
| 4,168,192 | 9/1979 | Nyberg . | |
| 4,207,364 | 6/1980 | Nyberg . | |
| 4,483,338 | 11/1984 | Bloom et al. | 606/50 |
| 4,516,972 | 5/1985 | Samson . | |
| 4,522,212 | 6/1985 | Gelinas et al. | 607/122 |
| 4,563,181 | 1/1986 | Wijayarathna et al. . | |
| 4,590,950 | 5/1986 | Iwaszkiewicz et al. | 607/119 |
| 4,592,372 | 6/1986 | Beranek | 607/119 |
| 4,636,346 | 1/1987 | Gold et al. . | |
| 4,690,175 | 9/1987 | Ouchi et al. . | |
| 4,735,620 | 4/1988 | Ruiz . | |
| 4,817,613 | 4/1989 | Jaraczewski et al. . | |
| 4,842,590 | 6/1989 | Tanabe et al. . | |
| 4,863,442 | 9/1989 | DeMello et al. . | |
| 4,899,787 | 2/1990 | Ouchi et al. . | |
| 4,955,862 | 9/1990 | Sepetka . | |
| 5,037,404 | 8/1991 | Gold et al. . | |
| 5,115,818 | 5/1992 | Holleman et al. | 607/122 |
| 5,156,151 | 10/1992 | Imran . | |
| 5,254,107 | 10/1993 | Soltesz . | |
| 5,257,451 | 11/1993 | Edwards et al. . | |

FOREIGN PATENT DOCUMENTS

| | | | |
|---|---|---|---|
| 269095 | 6/1989 | German Dem. Rep. | 607/122 |
| 91/13648 | 3/1991 | WIPO . | |
| 91/17782 | 5/1991 | WIPO . | |

*Primary Examiner*—Lee Cohen
*Attorney, Agent, or Firm*—Lyon & Lyon LLP

[57] ABSTRACT

A catheter having an elongated polymeric body with hollow encircling ring electrodes thereon and a method of forming the same are provided by the invention. Ring electrodes are each connected to an external electrical circuit by wires extending through the lumen, the wires each passing through an aperture through a wall of the body and being connected to an interior surface of the ring electrode. The tubular body of the catheter is expanded into a tight interference fit with the interior surfaces of the ring electrodes by heating the body to a temperature approaching its glass transition temperature to permit relief of internal stresses.

7 Claims, 2 Drawing Sheets

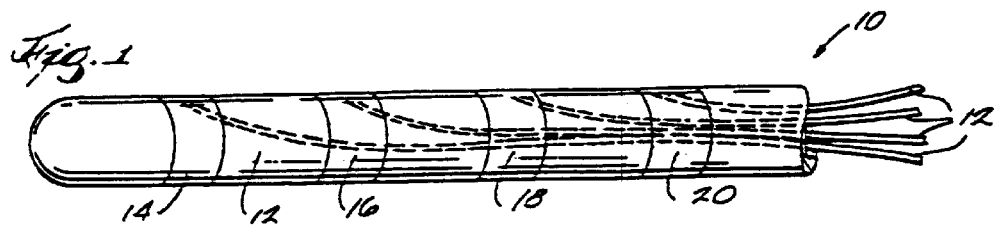
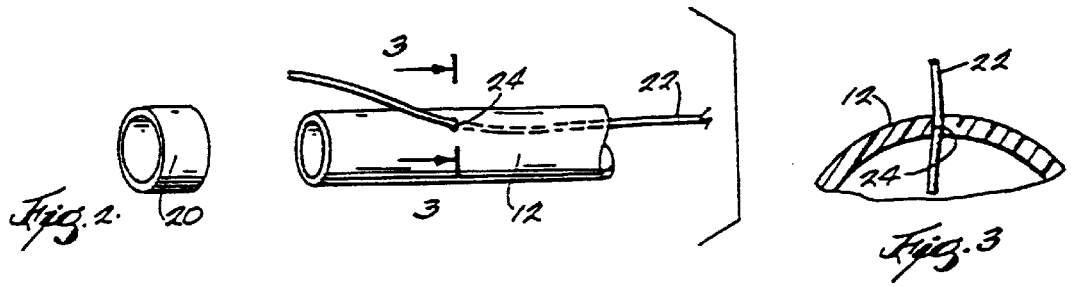
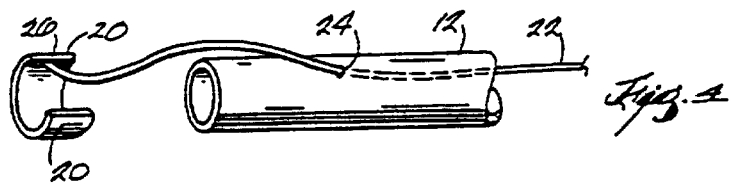
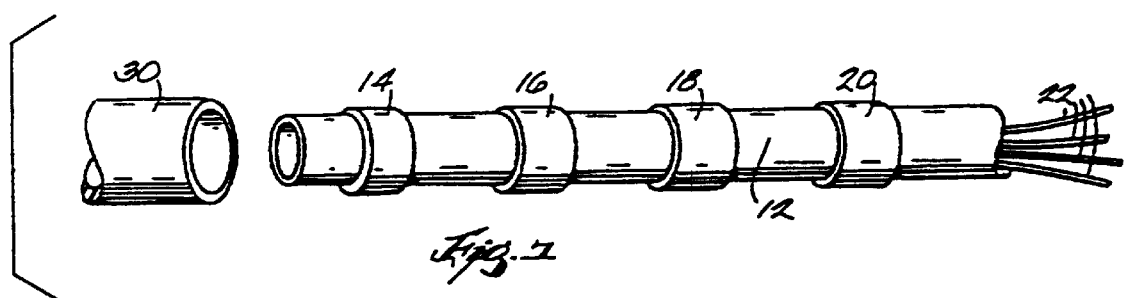
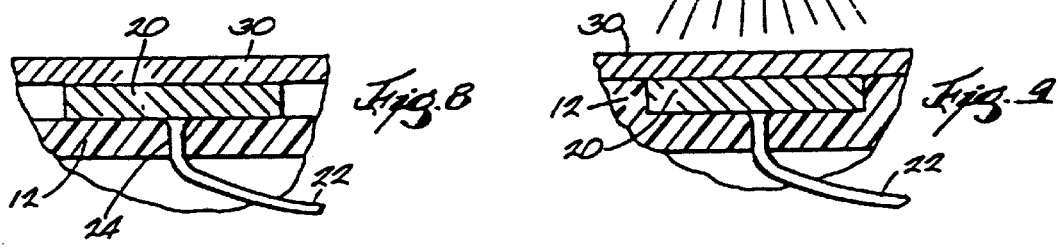

CATHETER HAVING RING ELECTRODES SECURED THEREON

This is a continuation of application Ser. No. 08/558,955 filed on Nov. 13, 1995, now abandoned; which is a divisional of Ser. No. 08/309,754 filed Sep. 21, 1994, now U.S. Pat. No. 5,524,337.

FIELD OF THE INVENTION

This invention relates to improved catheters having ring electrodes secured thereto and a method for securing such electrodes to a catheter body. More particularly, the invention relates to such electrodes and methods related to catheters intended for endocardial mapping and ablation systems.

BACKGROUND OF THE INVENTION

Various catheters have been provided for endocardial mapping and ablation. Such catheters are generally formed from an elongated hollow flexible tubular body having at least one lumen extending through the length thereof. Often, such catheters have a plurality of electrodes spaced along a surface thereof. In the past, such electrodes have generally been adhesively adhered to the catheter body. The procedures for adhering ring electrodes to the catheter body have heretofore been time consuming and have required a high degree of skill on the part of the assembler of such catheters. Also, adhesive often becomes applied to the electrode ring surface thereby reducing the electrically conductive usable sensing area. Thus, a need has existed for improved catheters containing ring electrodes and methods for producing the same.

SUMMARY OF THE INVENTION

It is a principal object of the invention to provide a method of securing ring electrodes around a tubular catheter body which minimizes or eliminates the need for adhesives. It is a further important object to provide catheters having ring electrodes non-adhesively secured thereto.

In accordance with an important aspect of the invention, heat and/or pressure expansion of catheter tubing is utilized to mechanically lock ring electrodes in place thereon. In accordance with a related aspect of the invention, tubing is provided which contains internal stresses such that when the tubing is subjected to an elevated temperature, it returns to a larger outer diameter, thus tightly engaging a ring electrode or plurality thereof encircling the tubing. In accordance with a still further aspect of the invention, the ring electrodes are placed in position encircling a catheter tubing segment and the tubing is then subjected to a temperature approaching its glass transition temperature, thus allowing it to relieve stresses or relax and expand to an increased diameter.

In accordance with a still further aspect of the invention, an internal gas pressure can be applied within the lumen of a catheter while it is being heated to assist in rapid expansion of the tubing. In accordance with a yet further aspect of the invention heat and gas pressure within a catheter lumen can be utilized as the sole or principal force to cause expansion of the catheter body.

In accordance with a still further aspect of the invention, the assembly which includes a catheter body and a plurality of encircling ring electrodes may be placed in a PTFE capture tube or mold and the assembly heated while contained therein. In accordance with a yet further aspect of the invention, the tube, after expanding, tightly engages a ring, which after the expansion step, is locked in a circumferential groove in the exterior surface of the tubing.

Briefly, a catheter having an elongated polymeric body with hollow encircling ring electrodes thereon and a method of forming the same are provided by the invention. Ring electrodes are each connected to an external electrical circuit by wires extending through the lumen, the wires each passing through an aperture through a wall of the body and being connected to an interior surface of the ring electrode. The tubular body of the catheter is expanded into a tight interference fit with the interior surfaces of the ring electrodes by heating the body to a temperature approaching its glass transition temperature to permit relief of internal stresses.

Still further objects and advantages of the invention will become apparent from the following detailed description and accompanying claims and drawings.

BRIEF DESCRIPTION OF THE DRAWINGS

FIG. 1 is a fragmentary perspective view of a distal tip portion of a catheter in accordance with the invention;

FIG. 2 is a fragmentary perspective view showing a section of tubing, a lead wire and a ring electrode prior to assembly thereof;

FIG. 3 is a fragmentary sectional view taken along line 3—3 of FIG. 2;

FIG. 4 is a fragmentary perspective view of the components of FIG. 2 showing a further step in the assembly thereof;

FIG. 5 is a fragmentary perspective view showing the parts of FIG. 2 in assemble relationship prior to the expansion of the tubing;

FIG. 6 is a fragmentary sectional view taken along line 6—6 of FIG. 5;

FIG. 7 is a fragmentary perspective view showing a plurality of ring electrodes on a catheter tubing section together with a capture tube used during the expansion process in accordance with the invention;

FIG. 8 is a sectional view showing the capture tube and catheter components in place for expansion thereof;

FIG. 9 is a fragmentary sectional view showing the components during a heating step; and, FIG. 10 is a perspective view of a heating device usable in connection with the invention.

DETAILED DESCRIPTION OF A PREFERRED EMBODIMENT

Figure 10:
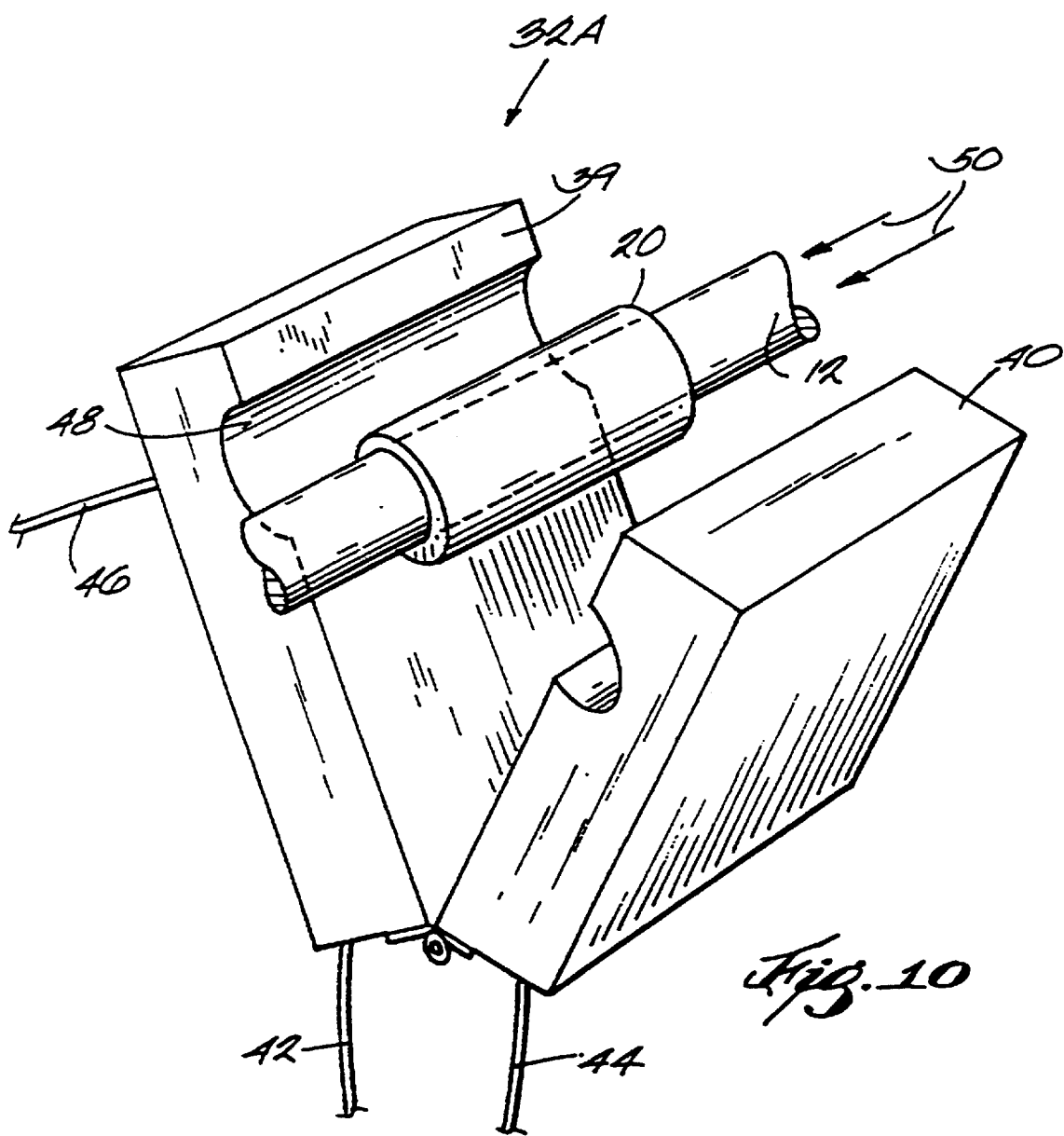

Referring more particularly to FIG. 1, there is seen a distal tip section 10 of a catheter formed in accordance with the invention. Catheter 10 includes a hollow tubular body portion 12 and a plurality of encircling ring electrodes 14, 16, 18 and 20.

Each of the electrodes is connected to a lead wire 22 for connection thereof to an electrical circuit of a type that varies in accordance with the intended use of the catheter. Such circuits may include monitoring circuits for measurement of electrical activity within a living body or may include a source of electrical power for an ablation catheter. Alternatively, the circuit may be of a type devised to provide electrical impulses for pacing or other diagnostic or therapeutic applications. Further, in some cases, ring electrodes may be provided for purposes of radiographic marking. In such cases, the lead wires 22 may be omitted. The present invention, thus, has applicability to formation of catheters of numerous types where it is desired to provide encircling ring electrodes.

Referring to FIG. 2, there is shown one of the electrode rings 20 for purposes of illustration. In this embodiment, an opening 24 is provided in the tubular body 20 on which ring 20 is to be placed. As best seen in FIG. 4, lead wire 22 can be soldered or otherwise secured to an interior surface of ring 20 by means of a connective joint 26. The ring 20 is seen in FIG. 5 in place over the unexpanded tube 12 with wire 22 extending into the central lumen thereof.

As seen in FIG. 7, a plurality of encircling rings 12, 16, 18 and 20 are positioned over the unexpanded tubular body 12. A confining mold in the form of a capture tube 30 as seen in FIG. 8. Capture tube 30 has an inner diameter approximately equal to the outer diameter of encircling rings 14–20. Mold or capture tube 30 is preferably a hollow tube formed of PTFE. Heat for expanding tubular body 12 is applied by means of a heating device 32 which may be in the form of a heated die or a stream of forced flow heated air.

Various heating devices can be used to heat the catheter body 12. An example is shown in FIG. 10. In FIG. 10 a heating element 32A is formed from two hinged metallic block components 39 and 40. The blocks may be heated by resistance heaters positioned internally and supplied by electrical leads 42 and 44, respectively. A thermocouple is also preferably located within either or both of components 39 and 40 and connected to a temperature monitoring and control circuit by means of a lead 46. Such a control circuit can be used in accordance with known technology to control the temperature of mold blocks 39 and 40 within a desired range of elevated temperatures. Components 39 and 40 are provided with mating semi-cylindrical mold cavities 48 and 49 adapted to fit closely over a capture tube 30.

It has generally been found suitable to heat the tubular body 12 to a temperature in the range of about 200° to 350° F., depending on the glass transition temperature of the particular plastic materials being used. Such temperatures have been found to effectively expand the catheter segments without fusion or loss of integrity of the tubular material. In most cases, a heating interval of about 10 to 20 seconds has been found effective.

The preferred method of introducing pressurized air into single lumen tubing entails sealing the proximal end of the assembly with electrical wires extending through it using a pressure fitting. A short section of a rigid properly sized tubing, for example, stainless steel tubing, is utilized to support the interior of the tube lumen from collapsing. The distal end of the tube is also supported with an internal rigid support tube. The distal end is connected by means of a pressure resistant seal to an external source of pressurized gas. It will be appreciated that in the event that a polymeric tube is used that does not contain internal stresses, the tube may be expanded by the application of heat and internal gas pressure alone.

In addition to the conduction heating through utilizing the mold shown in FIG. 10, heating can be accomplished in alternative ways. For example, convection heating can be employed utilizing a source of hot air to transfer heat to the assembly. Such heat can be applied to a small section of the unexpanded tubing inside the capture tube and slowly moved along the tubing length as expansion occurs. When using Pebax®, a polyether/polyamide block copolymer, as the expandable tubing, it is preferred that the hot air be provided at approximately 320° F. This higher temperature speeds up the expansion process by increasing the heat gradient through the insulating material used for a capture tube. This same technique can be utilized by providing infrared heat as the source of expansion energy.

Preferably pressurized air 50 is introduced into the inner lumen of tubular body 12 during the heating step. The resultant interior pressure ensures rapid and complete expansion of the tubular body.

To form the tubular body 12, a single lumen tubing is extruded to a dimension (outer diameter) that is slightly less than that required for the inner diameter of an electrode ring to pass through. Preferably the tubing is extruded with a long cone length just prior to being quenched in a water bath. This extrusion process locks in substantial stresses in the polymeric material forming the tubing that causes the same to expand in outer diameter and shrink in length when the tubing is subjected to temperatures approaching its glass transition temperature (Tg). Increasing the length of the cone used in the extrusion process increases the internal stresses within the polymer forming the tubing, particularly those related to elongative or linear stresses. Maintaining a very cold water quenching bath also is beneficial in rapidly quenching the material to lock in the stresses.

In addition to the polyether/polyamide block copolymer mentioned above, other polymers can be used in the practice of the invention. Examples of suitable thermoplastic materials polyolefins, polystyrene, acetals, acrylics, ethylene vinyl acetate, polyamides, PVC, polyurethanes, silicones and PTFE.

The following Example illustrates a preferred embodiment of the invention. It will be understood that numerous modifications of the materials, process conditions and dimensions provided can be made by those skilled in the art.

EXAMPLE

To make a 6 French catheter distal assembly, metal rings having the dimensions 0.077" OD and 0.069" ID are used as electrodes. An unexpanded Pebax® tube having a dimension of 0.069" OD and 0.042" ID is provided. The unexpanded tube is measured, marked and punctured at specific spots for the electrical wires to pass through as shown in FIG. 2. The wire is attached to the ring electrodes at this point when the wires are threaded through the holes in the tube wall. Because the tube is undersized and flexible, the rings easily slide over the tube. The rings are placed adjacent to the holes through which the wires pass. Just prior to placing the rings over the holes in the tubing, adhesive may be placed over the holes to occlude them once the rings are seated over them.

Once all the rings are in place as shown in FIG. 7, the capture tube can be placed over the assembly. The capture tube (in this case Teflon®, (PTFE), 0.120" OD and 0.080" ID) will retain its dimensions through the process. Pressurized air is introduced into the single lumen distal tubing as follows: The proximal end of the assembly with the electrical wires is sealed using a pressure fitting to seal the lumen end. The tube lumen is prevented from collapsing by temporarily supporting it internally using a short section of properly sized, rigid tubing such as stainless steel tubing. The distal end is also sealed using a pressure fitting with an internal rigid support tube. The distal pressure seal is connected to the pressure source.

When the assembly is pressurized, the assembly is exposed to the hot air source set for 320° F. in this case, for Pebax®, starting at one end of the assembly. As the section heats, the Pebax® expands and comes up to the ID of the capture tube (0.080"). As the expansion occurs, the assembly is slowly moved toward the other end of the assembly, to cause continuous expansion as it is moved. Once expansion is complete, the assembly is cooled. The pressure fittings are removed and the tube and ring assembly are removed from the capture tube. The distal end section is cut off as the tube section held by the pressure seal is unexpanded. The final tube dimensions are now 0.080" OD and 0.059" ID. The outer diameter of the tube in this case is slightly larger than the ring electrode and will physically hold it in place. In practice, it is preferred, prior to installation of the ring electrodes on the tube that the proximal end portion be expanded for approximately one inch. This is done because the section will not expand when it is held by a pressure seal. Any unexpanded end section of the tube is cut off prior to expansion of further sections.

While preferred embodiments of the invention have been shown for purposes of modification, it will be apparent to those skilled in the art that various modifications can be made falling within the true scope of the appended claims.

What is claimed is:

1. A catheter, comprising:

an elongated body including a wall region encircled by a metallic ring electrode, the metallic ring electrode having an interior surface; and a conductor having a first end passing through the wall region and connected to the interior surface of the metallic ring electrode, and a second end adapted for connection to an external circuit;

wherein the wall region includes an internally stressed thermoplastic material, which has been expanded to engage the interior surface to mechanically lock the metallic ring electrode to the elongated body, the thermoplastic material of the wall region being, after expansion, substantially free of internal stress.

2. A catheter according to claim 1 wherein the wall region is encircled by several metallic ring electrodes, each one mechanically locked to the elongated body by expansion of the thermoplastic material, which, after expansion, is substantially free of internal stress.

3. A catheter, comprising:

an elongated body including a wall region encircled by a metallic ring electrode, the metallic ring electrode having an interior surface; and a conductor having a first end passing through the wall region and connected to the interior surface of the metallic ring electrode, and a second end adapted for connection to an external circuit;

wherein the wall region includes an internally stressed polymeric material, which has been expanded to engage the interior surface to mechanically lock the metallic ring electrode to the elongated body, the polymeric material of the wall region being, after expansion, substantially free of internal stress.

4. A catheter, comprising:

an elongated body including a wall region encircled by a metallic ring electrode, the metallic ring electrode having an interior surface; and a conductor having a first end passing through the wall region and connected to the interior surface of the metallic ring electrode, and a second end adapted for connection to an external circuit;

wherein the wall region includes an internally stressed polymeric material, which has been expanded by heat to engage the interior surface to mechanically lock the metallic ring electrode to the elongated body, the polymeric material of the wall region being, after expansion by heat, substantially free of internal stress.

5. A catheter, comprising:

an elongated body including a wall region encircled by a metallic ring electrode, the metallic ring electrode having an interior surface; and a conductor having a first end passing through the wall region and connected to the interior surface of the metallic ring electrode, and a second end adapted for connection to an external circuit;

wherein the wall region includes an internally stressed polymeric material, which has been expanded by heat and pressure to engage the interior surface to mechanically lock the metallic ring electrode to the elongated body, the polymeric material of the wall region being, after expansion by heat and pressure, substantially free of internal stress.

6. A catheter according to claim 1 or 3 or 4 or 5, wherein the conductor is a wire.

7. A catheter according to claim 3 or 4 or 5 wherein the wall region is encircled by several metallic ring electrodes, each one mechanically locked to the elongated body by expansion of the polymeric material, which, after expansion, is substantially free of internal stress.

* * * * *